United States Patent
Roundy et al.

(10) Patent No.: US 12,214,154 B1
(45) Date of Patent: Feb. 4, 2025

(54) VALVE AND RELATED METHODS

(71) Applicant: JNM Medical LLC, Gilbert, AZ (US)

(72) Inventors: James Roundy, Gilbert, AZ (US); Neil Roundy, Eugene, OR (US)

(73) Assignee: James Roundy, Gilbert, AZ (US)

( * ) Notice: Subject to any disclaimer, the term of this patent is extended or adjusted under 35 U.S.C. 154(b) by 0 days.

(21) Appl. No.: 18/405,795

(22) Filed: Jan. 5, 2024

(51) Int. Cl.
| | |
|---|---|
| *A61M 39/24* | (2006.01) |
| *F16K 15/04* | (2006.01) |
| *F16K 15/18* | (2006.01) |
| *F16K 31/06* | (2006.01) |
| *F16K 31/08* | (2006.01) |

(52) U.S. Cl.
CPC ..... *A61M 39/24* (2013.01); *A61M 2039/2473* (2013.01); *A61M 2039/248* (2013.01); *F16K 15/04* (2013.01); *F16K 15/1823* (2021.08); *F16K 31/0665* (2013.01); *F16K 31/08* (2013.01); *F16K 31/084* (2013.01); *F16K 31/086* (2013.01)

(58) Field of Classification Search
CPC .......... A61M 39/24; A61M 2039/2473; A61M 2039/248; A61M 39/26; F16K 15/00; F16K 15/02; F16K 15/04; F16K 15/048; F16K 15/18; F16K 15/182; F16K 15/1823; F16K 31/00; F16K 31/003; F16K 31/02; F16K 31/06; F16K 31/08; F16K 31/084; F16K 31/086; F16K 31/0665; F16K 31/0627; F16K 31/0631; F16K 31/0634; F16K 31/0637; F16K 31/082; F16K 31/088; F15B 2013/0448

USPC .............................................. 251/65, 129.14
See application file for complete search history.

(56) References Cited

U.S. PATENT DOCUMENTS

| | | |
|---|---|---|
| 939,211 A | 11/1909 | Brown |
| 2,434,167 A | 1/1948 | Knoblauch |
| 2,598,009 A | 5/1952 | Peeps |
| 2,646,071 A | 7/1953 | Wagner |

(Continued)

FOREIGN PATENT DOCUMENTS

| | | |
|---|---|---|
| GB | 2249610 A | 10/1990 |
| GB | 2418239 A | 3/2006 |

(Continued)

OTHER PUBLICATIONS

RectusRegional, "TEMA—Hydraulik-Kupplung mit Druckentlastung—FF-Serie." https://www.youtube.com/watch?v=TVBmEjNmhu8, accessed as early as Jul. 2, 2022.

(Continued)

*Primary Examiner* — Nathan R Price
*Assistant Examiner* — Anna E Goldberg-Richmeier
(74) *Attorney, Agent, or Firm* — IPTechLaw

(57) ABSTRACT

Implementations of a valve may include a flow tube having a seat and a channel for transporting a flow downstream from an inlet to an outlet, a magnet disposed circumferentially around the flow tube at a first location, a movable magnet disposed circumferentially around the flow tube, the movable magnet movable between the inlet of the flow tube and the first location, and a plug disposed in the channel, the plug movable between an open position and a closed position in which the plug abuts the seat. The movable magnet may be configured to move the plug between the open position and the closed position.

9 Claims, 6 Drawing Sheets

(56) References Cited

U.S. PATENT DOCUMENTS

| | | |
|---|---|---|
| 2,660,456 A | 11/1953 | Meddock |
| 2,666,656 A | 1/1954 | Bruning |
| 2,667,895 A | 2/1954 | Pool et al. |
| 2,792,194 A | 5/1957 | Huck |
| 2,939,475 A | 6/1960 | Roach |
| 3,026,903 A | 3/1962 | Roach |
| 3,104,088 A | 9/1963 | Cator |
| 3,170,667 A | 2/1965 | Szohatzky |
| 3,174,508 A | 3/1965 | Zahuranec |
| 3,212,539 A | 10/1965 | Felix |
| 3,407,827 A | 10/1968 | Follett |
| 3,417,781 A | 12/1968 | Gregg |
| 3,495,620 A | 2/1970 | Raimondi et al. |
| 3,544,063 A | 12/1970 | Barlow et al. |
| 3,731,670 A * | 5/1973 | Loe ............... A61F 6/24 128/831 |
| 3,850,189 A | 11/1974 | Follett |
| 3,862,641 A | 1/1975 | Follett |
| 4,060,219 A | 11/1977 | Crawford |
| 4,114,853 A | 9/1978 | Medvick |
| 4,543,994 A | 10/1985 | Johnson et al. |
| 4,672,998 A | 6/1987 | Kozak, III |
| 4,865,588 A | 9/1989 | Flinchbaugh |
| 4,921,008 A | 5/1990 | Foster |
| 4,929,236 A * | 5/1990 | Sampson ............... A61M 39/12 604/905 |
| 5,255,714 A | 10/1993 | Mullins |
| 6,385,804 B1 | 5/2002 | Barber et al. |
| 7,252,112 B1 | 8/2007 | Imler et al. |
| 8,795,256 B1 | 8/2014 | Smith |
| 9,188,569 B2 | 11/2015 | Graham |
| 9,568,135 B2 | 2/2017 | Lehmann et al. |
| 2007/0066965 A1 | 3/2007 | Coambs et al. |
| 2008/0035222 A1 | 2/2008 | Fraser |
| 2008/0143098 A1 | 6/2008 | Zimmerman et al. |
| 2009/0288663 A1 | 11/2009 | East |
| 2011/0084474 A1 | 4/2011 | Paden et al. |
| 2012/0286185 A1 | 11/2012 | Spolski |
| 2013/0276923 A1 | 10/2013 | Wolff et al. |
| 2014/0001745 A1 | 1/2014 | Lehmann et al. |
| 2014/0318650 A1 | 10/2014 | Wolff et al. |
| 2015/0362111 A1 | 12/2015 | Konishi |
| 2017/0122456 A1 * | 5/2017 | Beyer .................. F16K 31/084 |
| 2017/0363240 A1 | 12/2017 | Ira et al. |
| 2019/0344041 A1 | 11/2019 | Gamard et al. |
| 2023/0347042 A1 * | 11/2023 | Fujioka ............... A61M 39/105 |

FOREIGN PATENT DOCUMENTS

| | | | |
|---|---|---|---|
| KR | 200444303 Y1 * | 5/2009 | ............. F16K 31/48 |
| RU | 2619520 C1 | 5/2017 | |
| WO | WO-2018087149 A1 * | 5/2018 | ............ A61M 39/10 |
| WO | WO-2024102640 A1 * | 5/2024 | ............ F16K 31/084 |

OTHER PUBLICATIONS

Micro Cupla Data Information Sheet, Stainless Steel Models, accessed as early as Jul. 2, 2022, pp. 1-4.

RU2619520C1, Published May 16, 2017 to Kabinov et al., Translation.

* cited by examiner

VALVE AND RELATED METHODS

BACKGROUND

1. Technical Field

Aspects of this document relate generally to valves and connectors, such as valves or connectors for connecting gas lines. More specific implementations involve connectors connecting oxygen or fluid lines to cannulas in a medical setting.

2. Background

Oxygen tubing and a connector are commonly encountered components for connecting oxygen delivery devices to flowmeters e.g., flowmeter on a portable oxygen concentrator, cylinder or wall connected flow meter. A tapered, barbed connector may be used with low pressure oxygen to connect the oxygen source to an oxygen delivery device, e.g., a cannula for use by a patient. A tubing line runs from the source to the connector and a cannula runs from the connector to the patient. To connect the cannula to the oxygen source, one end of the tubing is simply pushed over the tapered, barbed connector by hand.

SUMMARY

Implementations of a valve may include a flow tube having a seat and a channel for transporting a flow downstream from an inlet to an outlet, a magnet disposed circumferentially around the flow tube at a first location, a movable magnet disposed circumferentially around the flow tube, the movable magnet movable between the inlet of the flow tube and the first location, and a plug disposed in the channel, the plug movable between an open position and a closed position in which the plug abuts the seat. The movable magnet may be configured to move the plug between the open position and the closed position.

Implementations of valves may include one, all, or any of the following:

The plug may be a magnet.

The plug may be a magnetic material.

The seat may be upstream from the first location.

Implementations of the valve may include a housing. The housing may include a recess along an inner circumference of the housing. The movable magnet may be coupled within the recess.

The magnet may be configured to hold the plug in the closed position.

A first diameter of the channel upstream from the seat may be greater than a second diameter of the channel downstream from the seat.

A magnetic force between the magnet and the movable magnet may weaken as the plug is moved from the closed position to the open position.

Implementations of the valve may include a guard adjacent to the magnet. The guard may be upstream of the magnet.

The guard may be between the movable magnet and the magnet.

Implementations of a connector may include a first valve. The first valve may include a first flow tube having a first seat and a first channel for transporting a flow downstream from a first inlet to a first outlet, a first magnet disposed circumferentially around the first flow tube at a first location, a first movable magnet disposed circumferentially around the first flow tube, the first movable magnet movable upstream and downstream, and a first plug disposed in the first channel, the first plug movable between an open position and a closed position in which the first plug abuts the first seat. The first movable magnet may be configured to move the first plug between the open position and the closed position. Implementations of a connector may also include a second valve. The second valve may include a second flow tube having a second seat and a second channel for transporting a flow downstream from a second inlet to a second outlet, a second magnet disposed circumferentially around the second flow tube at a first location, a second movable magnet disposed circumferentially around the second flow tube, the second movable magnet movable upstream and downstream, and a second plug disposed in the second channel, the second plug movable between an open position and a closed position in which the second plug abuts the second seat. The second movable magnet may be configured to move the second plug between the open position and the closed position. The first valve may be configured to be in the open position and the second valve may be considered to be in the open position when the first valve is coupled to the second valve.

Implementations of connectors may include one, all, or any of the following:

The first seat may be upstream from the first magnet.

The second seat may be downstream from the second magnet.

The first valve may include a first housing having a first recess securing the first moveable magnet.

The first moveable magnet and the second moveable magnet may be configured to move away from one another to allow passage through the connector.

Implementations of a methods of adjusting a flow may include providing a first magnet and a second magnet around a flow tube, the flow tube having a channel and a seat, the channel having an inlet and an outlet, the seat located between the inlet and the outlet. The method may also include transporting a flow downstream through the channel from the inlet to the outlet, and moving the second magnet between the inlet and the first magnet to move a stopper between an open position and a closed position to adjust the flow in the channel.

Implementations of methods of adjusting a flow may include one, all, or any of the following:

The stopper may be in the closed position when the stopper abuts the seat.

A magnetic force between the first magnet and the second magnet may lessen as the second magnet moves the stopper to the open position.

The first magnet may be fixed at a first location downstream from the seat.

A second diameter of the channel downstream from the seat may be less than a width of the stopper.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended valve will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such valves and connectors, and implementing components and methods, consistent with the intended operation and methods.

Elements of the connectors disclosed herein that are non-movably fixed to one another may be bonded to one another through an adhesive. In other implementations, the elements non-movably fixed to one another may be formed of a single and continuous material.

Figure 1:
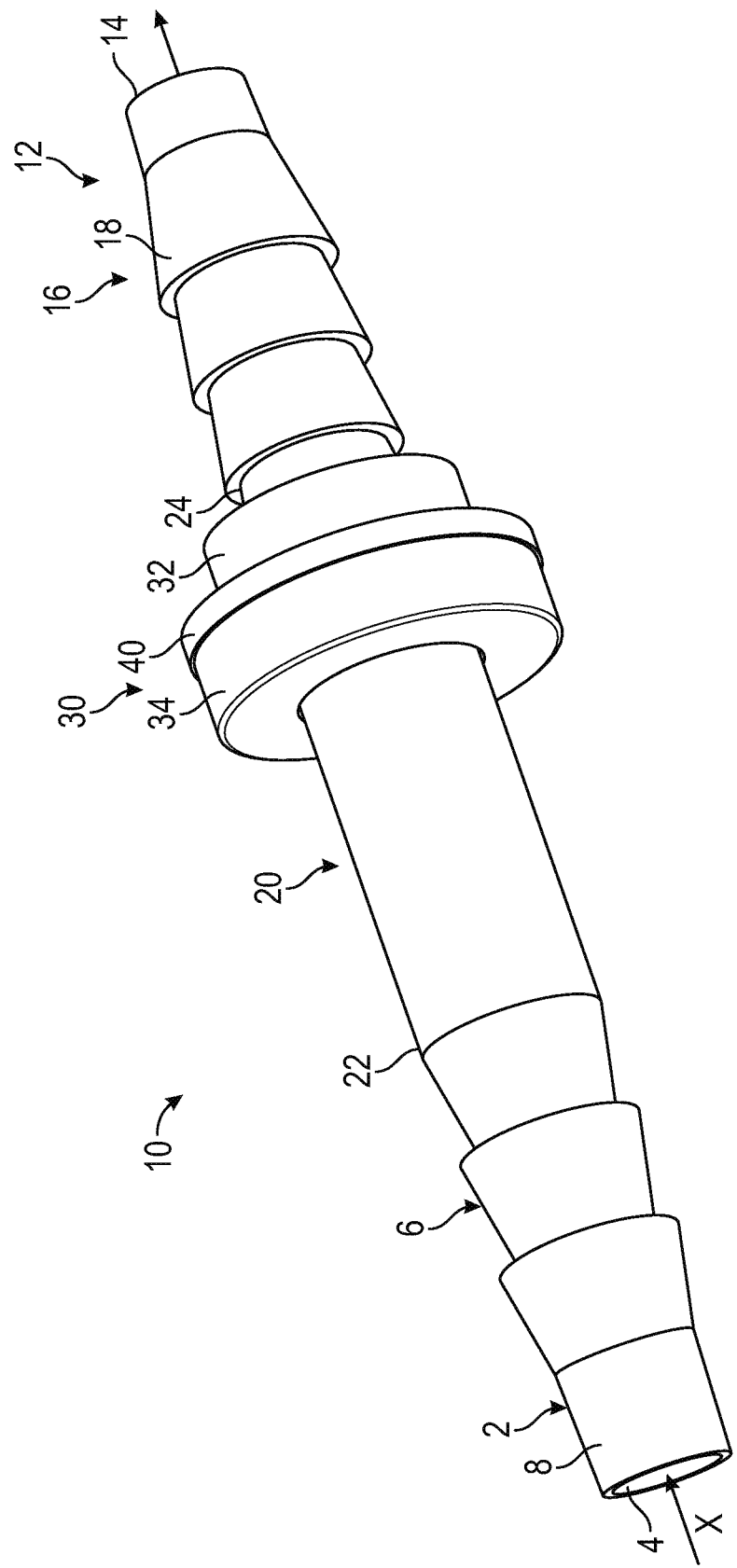
FIG. 1 is a perspective view of a connector with a valve in a closed position.

FIG. 1 illustrates a perspective view of a connector with a valve in a closed position. The connector of FIG. 1 is illustrated as having the housing removed. The connector 10 is configured to connect a source to a delivery device. For example, connector 10 is configured to connect an oxygen source to an oxygen delivery device such as a cannula. The connector 10 has an inlet end 2 including an inlet 4 and a barbed region 6 of an inlet tube 8, an outlet end 12 including an outlet 14 and a barbed region 16 of an outlet tube 18 and a flow tube 20 disposed between the inlet tube 8 and outlet tube 18. The flow tube 20 has an upstream end 22 and a downstream end 24. In various implementations, flow moves through the connector 10 from the inlet 4 to the outlet 14 in a direction X. Inlet end 2 of connector 10 is configured to be connected to a source, for example, an oxygen tank or oxygen source, and outlet end 12 of connector 10 is configured to be connected to an oxygen delivery device, for example, a cannula. Thus, oxygen flows from an oxygen source through connector 10 in direction X to an oxygen delivery device for use by a patient. Barbed regions 6, 16 may include one or a plurality of barbs. In various implementations, barbed regions 6, 16 may not include any barbs and may be, for example, tapered or threaded. In various implementations flow may also be configured to move in the opposite direction through the connector if the source is attached to the outlet 14 and the delivery device is attached to the inlet 4 (in such implementations the inlet 4 would then act as an outlet and the outlet 14 would then act as an inlet).

The connector 10 also includes a valve 30 which regulates flow through the connector 10. In the closed position, flow through the valve 30 is reduced or stopped. In the open position, flow passes through valve 30. Valve 30 includes a first magnet 32 circumferentially disposed around flow tube 20 and a second magnet 34 circumferentially disposed around flow tube 20. Magnet 32 is located near the downstream end 24 of flow tube 20 and second magnet 34 is located between magnet 32 and upstream end 22 of flow tube 20. First magnet 32 is stationary with respect to the direction of flow X and may be fixed to the downstream end 24 of flow tube 20. The location of first magnet 32 with respect to flow tube 20 may be adjusted as desired, however during operation, a location of first magnet 32 remains stationary with respect to the direction of flow X. In various implementations, the connector 10 includes a spacer or guard 40. In other implementations, the connector does not include a guard and allows the first magnet 32 to contact the second magnet 34. In implementations including a guard, the guard 40 is located upstream of magnet 32 and downstream from magnet 34. Guard 40 is circumferentially disposed about flow tube 20 and may be fixed to flow tube 20. In various implementations, guard 40 may be integral with or part of flow tube 20. Guard 40 may be designed to prevent first magnet 32 from contacting second magnet 34. In various implementations first magnet 32 may be stronger or weaker than second magnet 34 such that first magnet 32 draws second magnet 34 to first magnet 32. Magnets 32, 34 may be composed of various strengths, materials, sizes, and shapes as desired. As shown in FIG. 1, connector 10 is in a closed position. In the closed position, second magnet 34 is adjacent guard 40 due the attraction applied to second magnet 34 by first magnet 32. The guard 40 may prevent the first magnet 32 from colliding with he second magnet 34, thereby protecting the magnets.

In other implementations, the first magnet 32 may be replaced with a magnetic material. As used herein, magnetic materials refer to materials that are attracted to magnets but that are not magnets themselves. In such implementations, the second magnet may still be pulled downstream due to the magnetic force between the second magnet and the magnetic material.

Figure 2:
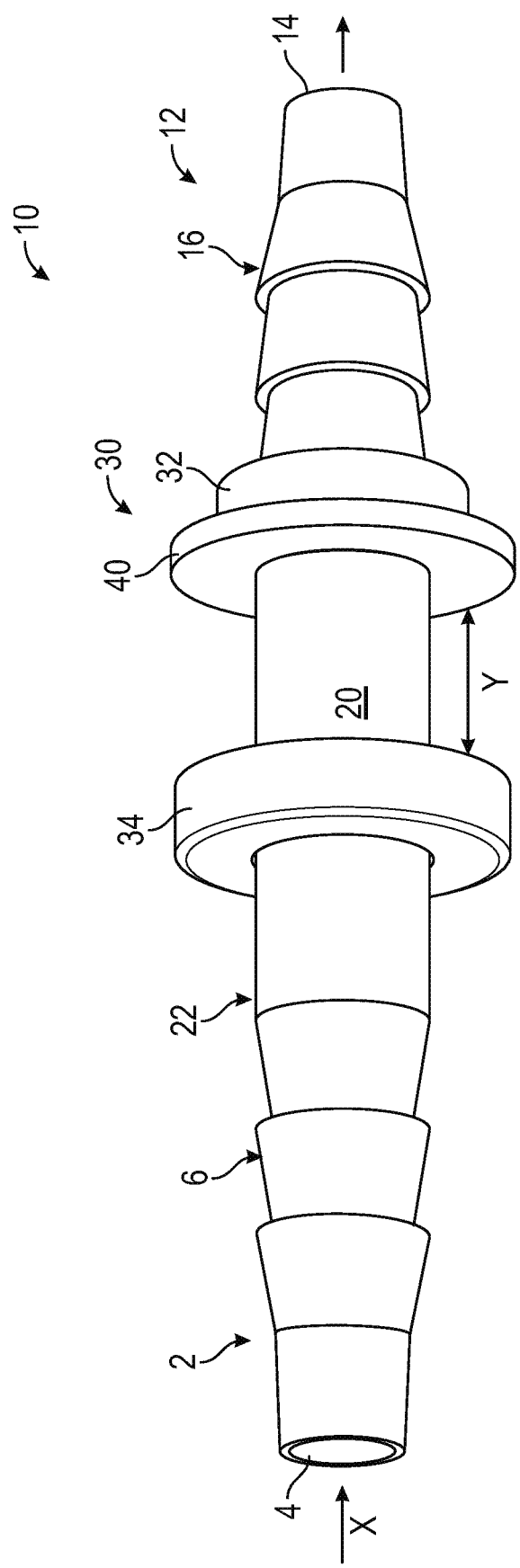
FIG. 2 is a front view of the connector of FIG. 1 with the valve in an open position.

Referring to FIG. 2, a front view of connector 10 with valve 30 in an open position is illustrated. The connector 10 is illustrated as having the housing removed. In the open position, second magnet 34 is spaced apart from guard 40. As shown, second magnet 34 has moved a distance Y upstream in the flow tube such that second magnet 34 is near the upstream end 22 of flow tube 20. Second magnet 34 may be pushed, pulled or otherwise moved upstream away from magnet 32 and guard 40 to move second magnet 34 from the closed position to an open position. In various implementations a small gap exists between an inner diameter of second magnet 34 and an outer surface of flow tube 20 in order to provide a loose fit or slip fit so second magnet 34 can move easily and with less friction with respect to flow tube 20. In various implementations, second magnet 34 may be moved manually and/or via a housing or other grip. When second magnet 34 is moved manually, a user applies sufficient force onto magnet 34 to move magnet 34 upstream. The force applied by the user must be stronger than the force applied by the first magnet 32 in order for the user to move second magnet 34 upstream.

Figure 3:
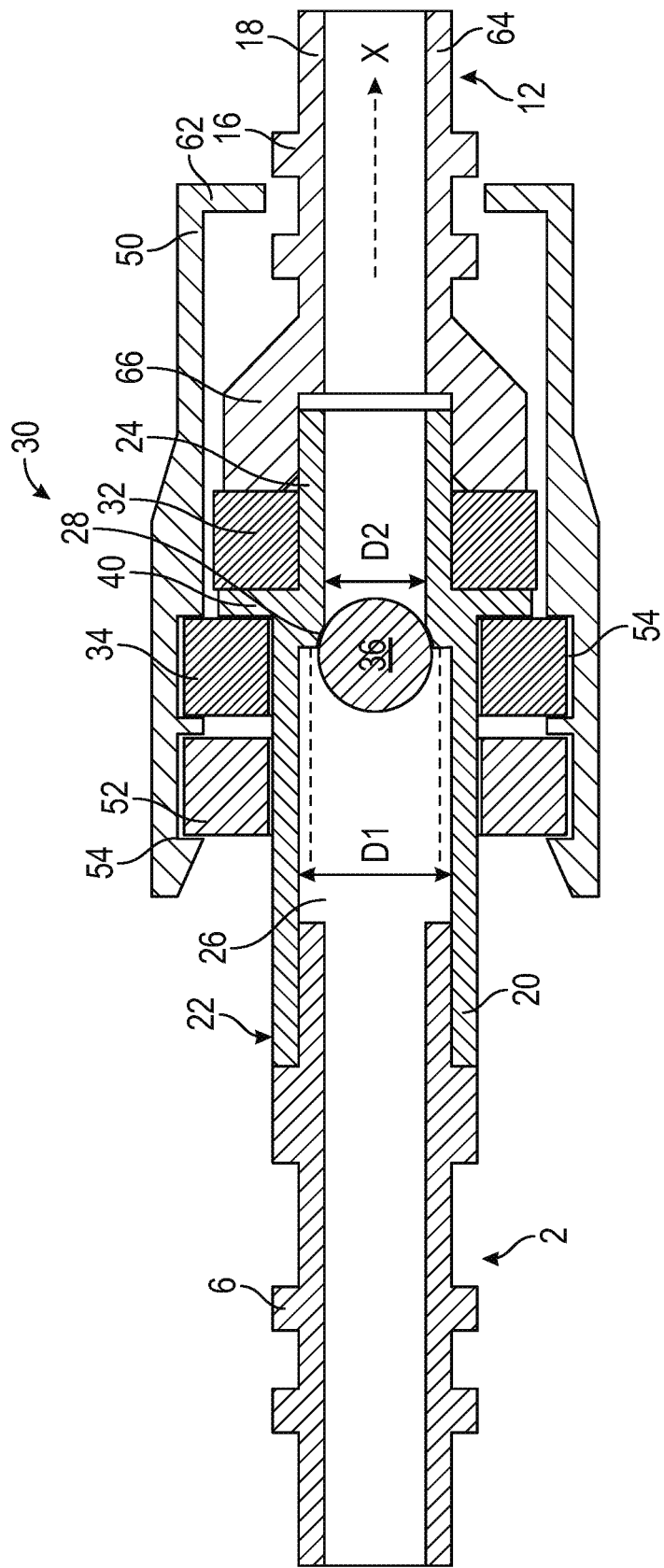
FIG. 3 is a cross sectional view of the connector of FIG. 1 with the valve in the closed position.

FIG. 3 shows a cross sectional view of connector 10 with valve 30 in the closed position. Flow tube 20 includes a channel 26 disposed therein and a valve seat 28 within the channel 26. Channel 26 runs from the upstream end 22 to the downstream end 24 of flow tube 20. The diameter of channel 26 may vary as desired to allow for variations of the open area. The implementation shown in FIG. 3 illustrates channel 26 having a plurality of diameters, a first diameter $D_1$ and a second diameter $D_2$. The first diameter $D_1$ extends from the upstream end 22 to the valve seat 28. The second diameter $D_2$ extends from the valve seat 28 to the downstream end 24.

Figure 4:
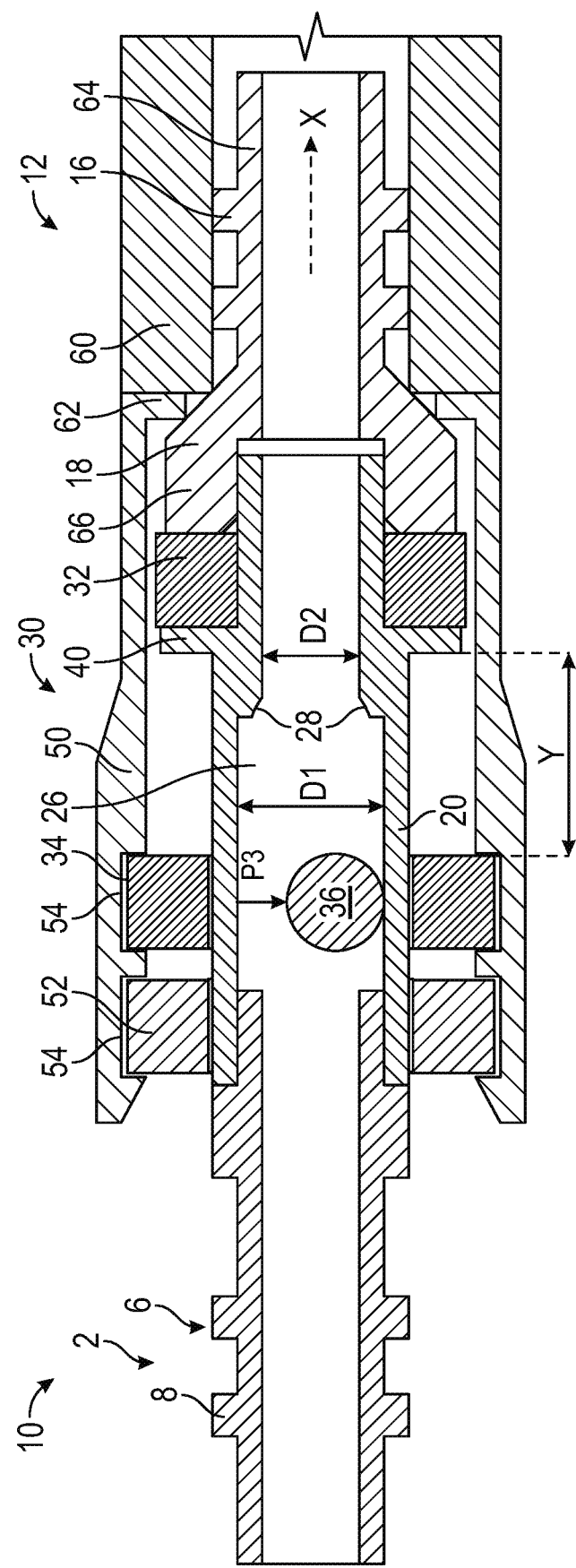
FIG. 4 is a cross sectional view of the connector of FIG. 2 with the valve in the open position.

Valve 30 includes a stopper or plug 36. The plug 36 may be a magnet or magnetic material. A geometry of the seat 28 is configured to accommodate the geometry of plug 36 so plug 36 fits securely against seat 28 to form a seal. In the closed position of valve 30, the plug 36 rests against seat 28 forming the seal. The seal prevents flow, e.g. gas or liquid, from traveling through the downstream end 24 of flow tube 20 while the valve 30 is in the closed position. In various implementations, the valve seat may include a seal or gasket (which may be rubber or another material) to improve the seal between the plug 36 and the seat 28. The valve seat 28 may be integral with an inner geometry of flow tube 20 or be an insert. As illustrated in FIGS. 3 and 4, an inner surface of flow tube 20 is shaped to form valve seat 28 which accommodates a spherical plug 36 in this implementation. In various implementations the shape of the plug or stopper and corresponding geometry of the seat may vary as desired. Similarly, the thickness of the guard 40 may also vary in order to specify how the plug or stopper sits on the seat.

In the closed position, second magnet 34 rests against guard 40 and plug 36 rests against seat 28. First magnet 32 exerts a magnetic force on second magnet 34 and plug 36 and pulls both towards first magnet 32. Thus, first magnet 32 draws second magnet 34 downstream to rest against guard 40 in the closed position. Second magnet 34 also exerts a magnetic force on plug 36 to keep plug 36 within channel 26 and to move plug 36 within the flow tube 20. Plug 36 naturally remains within the circumference of the second magnet 34 due to the magnetic fields of the second magnet 34. When in the open position, the plug 36 may contact an inner sidewall of the flow tube 20. In the closed position, the plug 36 may be centered over the seat 28. If plug 36 is ever forced out from the within the circumference of the second magnet 34, the plug 36 may be forced back into the center of the magnet by either pinning the magnet against the seat 28 or inlet tube 8 and forcing the second magnet 34 around the plug 36. Plug 36 is within the circumference of the second magnet 34 and also within the first diameter $D_1$ of channel 26 due to the magnetic forces applied by second magnet 34. Forces from second magnet 34 also move plug 36 upstream and downstream within the flow tube 20 as second magnet 34 moves upstream and downstream. Thus, when first magnet 32 draws second magnet 34 downstream to guard 40, second magnet pulls plug 36 downstream into seat 28 such that plug 36 sufficiently contacts seat 28 to form a seal. The position of second magnet 34 with respect to valve seat 28 and guard 40 ensures plug 36 maintains sufficient contact with seat 28. Once the plug 36 is brought to seat 28 by second magnet 34, a force from first magnet 32 on plug 36 may further enhance the seal, though the second magnet 34 may be the primary magnet that secures the plug 36 to the seat 28. Magnets 32, 34 are positioned so the forces exerted on plug 36 adequately seat plug 36 against seat 28 at low pressures to reduce or prevent flow. Further, in implementations where flow is entering the valve, the pressure of the flow against the plug 36 may further push the plug against the seat and improve the seal. The magnetic force between the second magnet 34 and the plug 36 is sufficient to open the valve by pushing the plug 36 against the direction of flow.

Referring still to FIG. 3, a housing 50 is circumferentially disposed around connector 10 and surrounds valve 30. The housing 50 is movable upstream and downstream in the direction of flow X and the housing 50 is configured to move second magnet 34 upstream and downstream in the direction of flow X. The housing 50 may include a retainer 52 to keep debris away from second magnet 34. The retainer 52 keeps debris out of the housing 50 and away from valve 30, thus preventing debris from impacting the movement of second magnet 34. A small gap may exist between an inner diameter of retainer 52 and an outer diameter of flow tube 20 so the retainer 52 can move easily and with less friction. The retainer 52 may be secured to the housing 50 in various ways or be held in place by retaining features configured into housing 50. In other implementations, the housing 50 may not include a separate retainer 52 and the second magnet 34 may serve as the retainer. As illustrated in FIG. 3, housing 50 has recesses 54 in an inner diameter of the housing 50 which serve as retaining features for retainer 52 and second magnet 34. Retainer 52 and second magnet 34 fit in recesses 54 such that retainer 52 and second magnet 34 move with the housing 50 parallel with the direction of flow X. The housing 50 and retainer 52 are also configured so that second magnet 34 does not move upstream beyond a set distance. In particular implementations, and as is illustrated by FIG. 3, the housing 50 includes a downstream end 62 that extends in towards the outlet tube 18. The downstream end 62 includes an opening therein through which the narrow portion 64 of the outlet tube is free to pass, however, the opening is smaller than the thick portion 66 of the outlet tube. In turn, when the housing is pushed towards the upstream end, the downstream end 62 may stop upstream movement of the housing when it contacts and is blocked by the thick portion 66. In other implementations the connector 10 may include a block at an upstream end of the connector that is configured to contact and block the upstream end of the housing or the retainer 52 to prevent further upstream movement of the housing. In various implementations, the housing 50 is arranged on connector 10 such that housing surrounds a portion of outlet tube 18 when the valve 30 is opened and closed. The housing 50 may also protect the valve 30 and connector 10 from bending or damage.

FIG. 4 shows a cross sectional view of connector 10 with valve 30 in the open position. Housing 50, second magnet 34 and plug 36 are a distance Y upstream with respect to the direction of flow X. In the open position, plug 36 no longer forms a seal against seat 28. Plug 36 is spaced apart from seat 28 allowing flow to pass through channel 26 into outlet end 12 of connector 10. In the open position, second magnet 34 is spaced apart from guard 40 and exerts a force on plug 36 so plug 36 stays within the circumference of the second magnet 34 and within the first diameter $D_1$ of channel 26.

As illustrated in FIG. 4, an end of a tube 60, for example, a cannula, is attached to the outlet end 12 of connector 10. The tube 60 is connected over the barbed region 16 of outlet tube 18. As tube 60 is attached to connector 10, tube 60 contacts the downstream end 62 of the housing 50 and pushes housing 50 upstream in the opposite direction of flow X. The manual force applied to housing 50 by tube 60 from a user attaching the tube 60 to connector 10 is sufficient to overcome the force of first magnet 32 attracting second magnet 34 thereto. As housing 50 moves upstream, second magnet 34 is forced upstream and the force second magnet 34 exerts on plug 36 unseats plug 36 from valve seat 28 and pulls plug 36 upstream. Thus, second magnet 34 and plug 36 move upstream a distance Y with housing 50. In various implementations, housing 50 may be moved manually and separately from tube 60 to move the valve 30 between closed and open positions. For example, housing 50 may be moved manually upstream just prior to attaching tube 60 to connector 10.

As the distance Y increases between first magnet 32 and second magnet 34, the force between first magnet 32 and second magnet 34 decreases because the magnetic force between magnets decreases as the distance between the magnets increases. The resulting decrease in force facilitates housing 50 remaining positioned upstream due to the opposing force applied by tube 60. The placement and attachment of tube 60 over barbed region 16 of outlet tube 18 provides a sufficient opposing force to maintain housing 50 upstream and to keep valve 30 open. The configuration of housing 50 ensures that second magnet 34 remains within a set distance to first magnet 32 to ensure that first magnet 32 exerts an attractive force on second magnet 34 sufficient to draw second magnet 34 downstream when opposing forces on housing 50 (by tube 60) are reduced or eliminated, e.g., when tube 60 is removed from outlet tube 18. In contrast, if housing 50 were, for example, spring-loaded downstream, the force exerted by housing 50 on tube 60 could negatively impact the coupling and be strong enough to push tube 60 off outlet tube 18. The spring force against tube 60 would increase as the housing 50 is moved upstream.

Referring now to FIGS. 3 and 4, when a user removes tube 60 from connector 10, the housing 50 retreats downstream due to the attraction force between first magnet 32 and second magnet 34. First magnet 32 attracts second magnet 34 thereto. Due to the attraction force between second magnet 34 and plug 36, plug 36 also moves downstream with second magnet 34 until valve 30 is in a closed position in which second magnet 34 rests against guard 40 and plug 36 securely contacts seat 28 thereby forming a seal to reduce or prevent flow from exiting flow tube 20. In various implementations, the first magnet 32 primarily attracts the second magnet 34 but may also attracts plug 36 downstream. As explained above, if the housing 50 were, for example, spring-loaded downstream, the spring force pushing to return housing 50 downstream may be too great, could apply undue pressure on tube 60 and jeopardize the coupling of tube 60 and connector 10.

In various implementations, a washer or spacer may be secured to a downstream end of housing 50 to accommodate for varying tube 60 designs to ensure housing 50 moves a sufficient distance to open the valve 30 by unseating plug 36 and allowing flow downstream.

In various implementations the thickness of guard 40 may vary to adjust the position or distance between first magnet 32 and second magnet 34. Additionally, spacers may be provided on either side of guard 40 or in lieu of guard 40 to provide desired spacing between first magnet 32 and second magnet 34. The spacers may be from 1/32 to 1/16 inch thick. The guard and spacers may also be used to adjust the force that holds plug 36 on seat 28 when the valve 30 is closed by adjusting the position of second magnet 34 with respect to plug 36 and the position of first magnet 32 with respect to plug 36. Reducing the distance between second magnet 34 and plug 36 and first magnet 32 and plug 36 will increase the force second magnet 34 and first magnet 32 apply to plug 36. Conversely, increasing the distance between second magnet 34 and plug 36 and first magnet 32 and plug 36 will decrease the force second magnet 34 and first magnet 32 apply to plug 36. In other implementations, the connector may not include guard 40 and the first magnet 32 may be configured to directly contact the second magnet 34.

In various implementations, inlet tube 8 mates with an inlet of flow tube 20 and may be secured or bonded to flow tube 20 after plug 36 is inserted into channel 26. For example, an outer diameter of the downstream end of inlet tube 8 may be coupled or bonded to an inner diameter of channel 26 on the upstream end 22 of flow tube 20. The diameter of inlet tube 8 may be selected such that plug 36 stays within channel 26 of flow tube 20 and cannot enter inlet tube 8. Thus, plug 36 moves inside channel 26 between the seat 28 and inlet tube 8. The plug 36 remains centered with respect to an inner diameter of second magnet 34 in channel 26. If, for example, an external force is applied to connector 10 and knocks plug 36 out of the inner diameter of second magnet 34, plug 36 may move within channel 26 between inlet tube 8 and seat 28 but will return to a stable position in the inner diameter of second magnet 34 due to the magnetic forces applied to plug 36 by second magnet 34.

Figure 5:
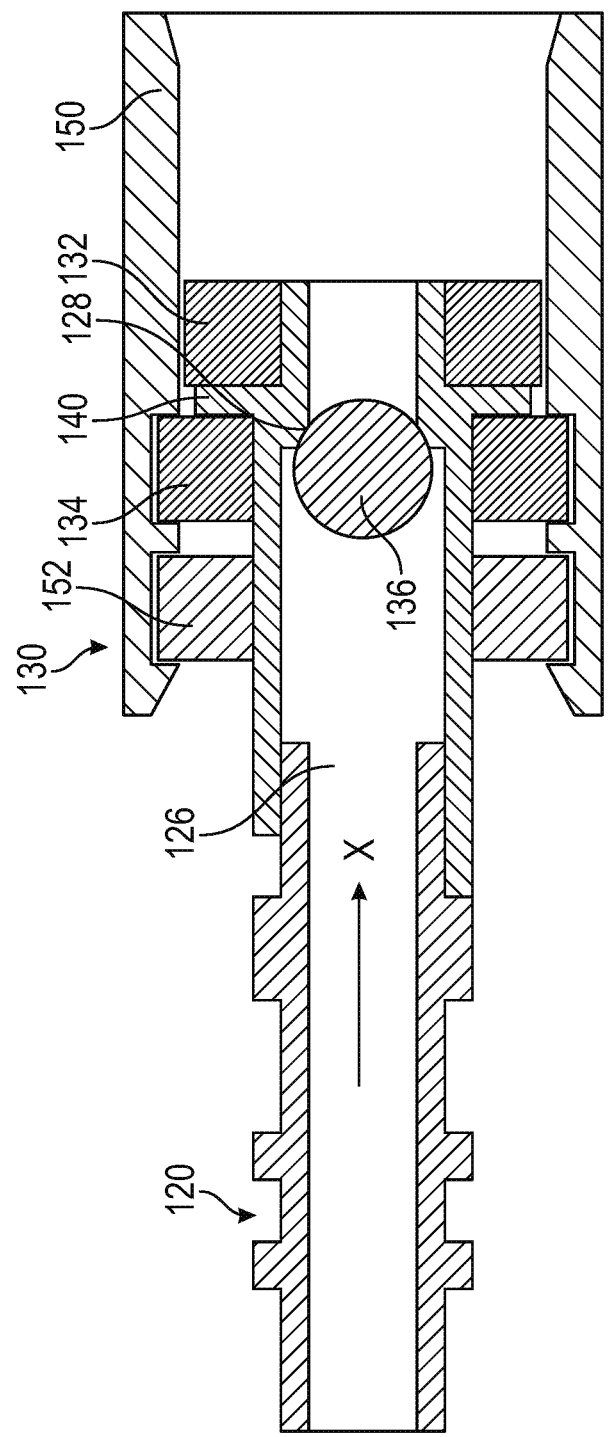
FIG. 5 is a cross sectional view of an implantation of a valve of a connector in a closed position.
Figure 6:
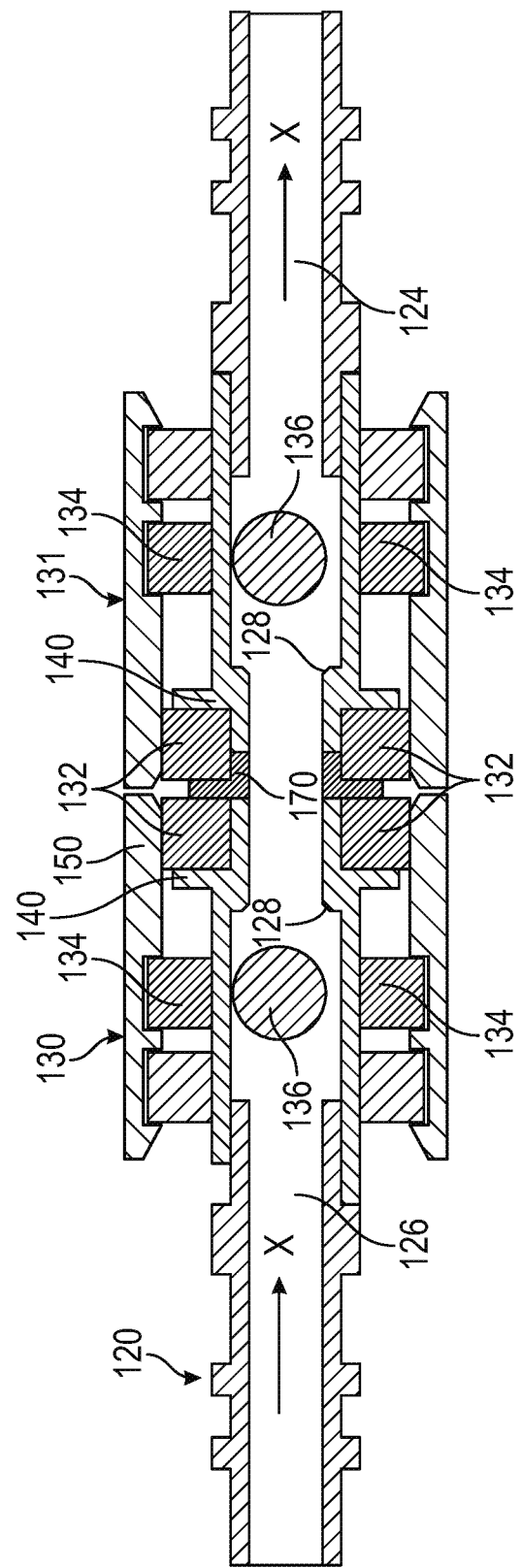
FIG. 6 is a cross sectional view of the connector in an open position.

Referring to FIG. 5, a cross sectional view of an implementation of a valve of a connector in a closed position is illustrated. Referring to FIG. 6, a cross sectional view of the connector in an open position is illustrated. The connector 100 includes two valves 130, 131 which regulate flow through the connector 100. In the closed position illustrated in FIG. 5, only valve 130 is illustrated. Flow through the valve 130 is reduced or stopped in FIG. 5. In the open position, illustrated in FIG. 6, flow passes through valves 130, 131. Valves 130, 131 are similar to valve 30 discussed above with similar features numbered similarly (i.e. "26" corresponds with "126") and working in a similar manner which may not be reiterated below.

Valves 130 and 131 each include a first magnet 132 circumferentially disposed around flow tube 120. Both first magnets are stationary with respect to the direction of flow X and may be fixed to flow tube 120. The locations of first magnets 132 with respect to flow tube 120 may be adjusted as desired, however during operation, a location of first magnets 132 remains stationary with respect to the direction of flow X. The connector 120 may include guards 140 which may be located between first magnets 132 and second magnets 134, circumferentially disposed about flow tubes 120, and may be fixed to flow tubes 120. The second magnets 134 are configured to slide along the flow tube 120 to open and close the valves 130, 131.

Valves 130, 131 include a stopper or plug 136. A geometry of seats 128 are configured to accommodate the geometry of plugs 136 so plugs 136 fit securely against seats 128 to form a seal. In the closed position of valves 130, 131 the plugs 136 rest against seats 128 forming the seal. The seal prevents flow, e.g. gas or liquid, from traveling through the downstream end 124 of flow tube 120 while the valves 130, 131 are in the closed position.

In the closed position, second magnet 134 may rest against guard 140 and plug 136 rests against seat 128, as illustrated in FIG. 5. First magnet 132 exerts a magnetic force on second magnet 134 and plug 136 so first magnet 132 draws second magnet 134 to rest against guard 140 in the closed position. Second magnet 134 also exerts a magnetic force on plug 136 to keep plug 136 within channel 126 and to move plug 136 within the flow tube 120. Forces from second magnet 134 also move plug 136 upstream and downstream in the flow tube 120 as second magnet 134 moves upstream and downstream. Thus, when first magnet 132 draws second magnet 134 to the guard 140, second magnet 134 pulls plug 136 downstream into seat 128 such that plug 136 sufficiently contacts seat 128 to form a seal. The position of second magnet 134 with respect to valve seat 128 and guard 140 ensures plug 136 maintains sufficient contact with seat 128. Once the plug 136 is brought to seat 128 by second magnet 134, a force from first magnet 132 on plug 136 may further enhance the seal. Magnets 132, 134 are positioned so the forces exerted on plug 136 adequately seat plug 136 against seat 128 at low or no pressures to reduce or prevent airflow.

Referring to FIG. 6, a cross section of connector 100 with valves 130, 131 in an open position is illustrated. Valve 130 and valve 131 are arranged end to end, such that first magnets 132 are proximal to one another. In the open position, second magnet 134 is spaced apart from guard 140 by a distance Y in the direction of the length of the flow tube 120. With respect to valve 130, housing 150 and second magnet 134 are moved upstream, whereas, with respect to valve 131, housing 150 and second magnet 134 are moved downstream. With respect to both valves 130, 131, housing 150 and second magnet 134 are moved away from first magnet 132 and guard 140. Housing 150 and second magnet 134 may be pushed, pulled or otherwise moved away from magnet 132 and guard 140 to move second magnet 134 from the closed position to an open position.

Valve 130 is coupled to valve 131 via a bridge 170 and housings 150. Housings 150 may have the same features as housings 50 discussed above. In various implementations each of the housings 150 may include a recess configured to receive a retainer 152 similar to the retainer 52 of FIG. 3. In other implementations, the housings may not include such a recess or retainer. Housings 150 are configured such that when valves 130, 131 are connected, housings 150 force the valves 130, 131 into an open position by pushing second magnets 134 and plugs 136 away from first magnets 132 and guards 140 as illustrated in FIG. 6. Thus, the configuration of the housings 150 and coupling of valve 130 to valve 131 places the connector 100 in an open position. When the valves 130 and 131 are disconnected from one another, valves 130, 131 move to a closed position in which plug 136 abuts seat 138 forming a seal that reduces or eliminates flow through flow tubes 120 as illustrated in FIG. 5. The valves 130, 131 move to the closed position because first magnets 132 exert a force on second magnets 134 drawing second magnets 134 and plugs 136 thereto as explained above. The orientation of the magnetic poles in valves 130 and 131 are arranged to achieve proper attraction forces. In various implementations, housing 150 may be biased towards the closed position in order to aid in closing valves 130, 131. In various implementations, connector 100 may be used advantageously when flow needs to be closed off from sources on both ends of flow tubes 120. For example, a patient may be connected to a drain tube to drain fluids through connector 100 into a collection bag. In this example, flow is drained from patient through valves 130, 131 and downstream to a collection bag. If connector 100 were to become disconnected, intentionally or unintentionally, the drain line from the patient would be automatically closed via valve 130 and the drain line to the collection bag would be closed via valve 131. Thus, connector 100 would prevent leakage from the patient's drain line and leakage from the collection bag in the event the drain line became disconnected from the collection bag.

In places where the description above refers to particular implementations of a connector or valve and implementing components, sub-components, methods and sub-methods, it should be readily apparent that a number of modifications may be made without departing from the spirit thereof and that these implementations, implementing components, sub-components, methods and sub-methods may be applied to other connectors or valves.

What is claimed is:

1. A connector comprising:
    a first valve comprising:
        a first flow tube having a first seat and a first channel for transporting a flow downstream from a first inlet to a first outlet;
        a first magnet disposed circumferentially around the first flow tube at a first location;
        a first movable magnet disposed circumferentially around the first flow tube, the first movable magnet movable upstream and downstream; and
        a first plug disposed in the first channel, the first plug movable between an open position and a closed position in which the first plug abuts the first seat, wherein the first movable magnet is configured to move the first plug between the open position and the closed position; and
    a second valve comprising:
        a second flow tube having a second seat and a second channel for transporting a second flow downstream from a second inlet to a second outlet;
        a second magnet disposed circumferentially around the second flow tube at a second location;
        a second movable magnet disposed circumferentially around the second flow tube, the second movable magnet movable upstream and downstream; and
        a second plug disposed in the second channel, the second plug movable between the open position and the closed position in which the second plug abuts the second seat, wherein the second movable magnet is configured to move the second plug between the open position and the closed position;
        wherein the first valve is configured to be forced into the open position when the first valve is coupled to the second valve.

2. The connector of claim 1, wherein the first seat is upstream from the first magnet.

3. The connector of claim 2, wherein the second seat is downstream from the second magnet.

4. The connector of claim 1, wherein the first flow tube extends through the first magnet and the second flow tube extends through the second magnet.

5. The connector of claim 1, wherein the first movable magnet and the second movable magnet are configured to move away from one another to allow passage through the connector.

6. A connector comprising:
    a first valve comprising:
        a first flow tube having a first seat and a first channel for transporting a flow downstream from a first inlet to a first outlet;
        a first magnet disposed circumferentially around the first flow tube at a first location;
        a first movable magnet disposed circumferentially around the first flow tube, the first movable magnet movable upstream and downstream; and
        a first plug disposed in the first channel, the first plug movable between an open position and a closed position in which the first plug abuts the first seat, wherein the first movable magnet is configured to move the first plug between the open position and the closed position; and
        a first housing coupled around the first moveable magnet; and
    a second valve comprising:
        a second flow tube having a second seat and a second channel for transporting a second flow downstream from a second inlet to a second outlet;
        a second magnet disposed circumferentially around the second flow tube at a second location;
        a second movable magnet disposed circumferentially around the second flow tube, the second movable magnet movable upstream and downstream; and
        a second plug disposed in the second channel, the second plug movable between the open position and the closed position in which the second plug abuts the second seat, wherein the second movable magnet is configured to move the second plug between the open position and the closed position;

a second housing coupled around the second moveable magnet;

wherein the first housing contacts the second housing when the first valve is coupled to the second valve;

wherein the first valve is configured to be in the open position and the second valve is considered to be in the open position when the first valve is coupled to the second valve.

7. The connector of claim 6, wherein the first seat is upstream from the first magnet.

8. The connector of claim 6, wherein the second seat is downstream from the second magnet.

9. The connector of claim 6, wherein the first movable magnet and the second movable magnet are configured to move away from one another to allow passage through the connector.

* * * * *